(12) United States Patent
Mor

(10) Patent No.: US 7,462,158 B2
(45) Date of Patent: Dec. 9, 2008

(54) BONE-GROWTH STIMULATOR

(76) Inventor: Amit Mor, 9 Smilanski Street, Rehovot 76446 (IL)

( * ) Notice: Subject to any disclaimer, the term of this patent is extended or adjusted under 35 U.S.C. 154(b) by 538 days.

(21) Appl. No.: 10/840,348

(22) Filed: May 7, 2004

(65) Prior Publication Data
US 2005/0251068 A1    Nov. 10, 2005

(51) Int. Cl.
A61H 1/00 (2006.01)
(52) U.S. Cl. .................................. 601/46; 482/148
(58) Field of Classification Search .............. 601/15, 601/26–29, 46, 70; 482/148
See application file for complete search history.

(56) References Cited

U.S. PATENT DOCUMENTS

| 3,867,929 | A | * | 2/1975 | Joyner et al. ............ 601/166 |
| 4,262,434 | A | * | 4/1981 | Michelotti ................ 36/67 D |
| 4,660,548 | A | * | 4/1987 | Bucher ..................... 601/61 |
| 5,018,511 | A | * | 5/1991 | Yokoi ....................... 601/84 |
| 5,103,806 | A |   | 4/1992 | Mcleod et al. |
| 5,113,850 | A | * | 5/1992 | Larremore et al. ......... 601/46 |
| 5,211,160 | A |   | 5/1993 | Talish et al. |
| 5,520,612 | A |   | 5/1996 | Winder |
| 5,730,705 | A |   | 3/1998 | Talish et al. |
| D448,920 | S | * | 10/2001 | Montross et al. .......... D2/954 |
| 6,432,070 | B1 |  | 8/2002 | Talish et al. |
| 6,464,654 | B1 | * | 10/2002 | Montgomery et al. ...... 601/46 |
| 6,979,287 | B2 | * | 12/2005 | Elbaz et al. ............... 482/148 |
| 2003/0153849 | A1 | | 8/2003 | Huckle et al. |
| 2004/0082886 | A1 | * | 4/2004 | Timpson .................. 601/15 |

FOREIGN PATENT DOCUMENTS

| WO | 96/20651 | 7/1996 |
| WO | 00/67846 | 11/2000 |
| WO | 03/090868 | 11/2003 |

* cited by examiner

*Primary Examiner*—Michael A. Brown
(74) *Attorney, Agent, or Firm*—Dekel Patent Ltd.; David Klein

(57) ABSTRACT

Apparatus including a bone-growth stimulator including a vibrating element housed in a hand-held housing and/or an osseous limb wrapping.

8 Claims, 3 Drawing Sheets

BONE-GROWTH STIMULATOR

FIELD OF THE INVENTION

The present invention relates generally to stimulation of bone growth, particularly by the application of vibration and inducement of mechanical strain in bone tissue.

BACKGROUND OF THE INVENTION

Numerous publications and patents disclose various methods of maintaining or promoting bone-tissue growth. For example, U.S. Pat. No. 5,103,806 to Clinton Rubin describes methods of promoting bone-tissue growth and bone maintenance by the application of relatively high frequency, relatively low level mechanical load to the bone tissue. The preferred frequency mentioned in that patent document is in the range of about 10-50 Hz, and the preferred peak-to-peak level of the mechanical load is sufficient to induce strain on the order of between about 50 and about 500 microstrain. Mechanical loading on bone tissue at strains of this level and induced within the frequency range set forth above can prevent bone loss and enhance new bone formation.

Rubin has also published many articles about the subject. Two pertinent examples are "Transmissibility of 15-Hertz to 35-Hertz Vibrations to the Human Hip and Lumbar Spine: Determining the Physiologic Feasibility of Delivering Low-Level Anabolic Mechanical Stimuli to Skeletal Regions at Greatest Risk of Fracture Because of Osteoporosis", Clinton Rubin, Malcolm Pope, J. Chris Fritton, Marianne Magnusson, Tommy Hansson, and Kenneth McLeod, Spine 2003; 28:2621-2627, and accessible as bme.sunysb.edu/bme/people/faculty/docs/crubin/2003-Spine-transmissibility.pdf. This study involves experiments to determine the degree to which high-frequency (15-35 Hz) ground-based, whole-body vibration are transmitted to the proximal femur and lumbar vertebrae of the standing human. The objective of the experiments is to establish if extremely low-level (1 g) mechanical stimuli can be efficiently delivered to the axial skeleton of a human. Under sterile conditions and local anesthesia, transcutaneous pins were placed in the spinous process of L4 and the greater trochanter of the femur of six volunteers. Each subject stood on an oscillating platform and data were collected from accelerometers fixed to the pins while a vibration platform provided sinusoidal loading at discrete frequencies from 15 to 35 Hz, with accelerations ranging up to 1 g peak-peak.

With the subjects standing erect, the results of the experiments showed transmissibility at the hip exceeded 100% for loading frequencies less than 20 Hz, indicating a resonance. However, at frequencies more than 25 Hz, transmissibility decreased to approximately 80% at the hip and spine. In relaxed stance, transmissibility decreased to 60%. With 20-degree knee flexion, transmissibility was reduced even further to approximately 30%. A phase-lag reached as high as 70 degrees in the hip and spine signals.

Another publication, "Inhibition of osteopenia by low magnitude, high-frequency mechanical stimuli", Clinton T. Rubin, Dirk W. Sommerfeldt, Stefan Judex and Yi-Xian Qin, Drug Discovery Today 6:848-858, August 2001, and accessible as bme.sunysb.edu/bme/people/faculty/docs/crubin/2001-DDT-bone-adapt.pdf, discusses the identification of anabolic agents for the treatment of metabolic bone disease. In searching for the osteogenic (bone-producing) constituents within mechanical stimuli, it was determined that high frequency (10-100 Hz) and low magnitude (<10 microstrain) stimuli were capable of augmenting bone mass and morphology, thereby benefiting both bone quantity and quality.

In all of the known prior art, the vibrations have been introduced by having the subject stand on floor-based vibration devices.

SUMMARY OF THE INVENTION

The present invention seeks to provide a novel bone-growth stimulator, as is described more in detail hereinbelow. The bone-growth stimulator may be used for humans and animals. The bone-growth stimulator may maintain or promote bone-tissue growth, and may be effective in the prevention of deep vein thrombosis. The bone-growth stimulator may also assist in the healing of muskoloskeletal injuries.

Contrary to the prior art, which attempts to induce vibration to the subject while standing on a vibration device, the present invention provides substantially more effective treatment by localizing the vibration, as is described hereinbelow.

There is thus provided in accordance with an embodiment of the present invention apparatus including a bone-growth stimulator including a vibrating element housed in a hand-held housing and/or an osseous limb wrapping.

In accordance with an embodiment of the present invention the vibrating element may include an oscillating element energized by an electrical power source. The electrical power source may be disposed in the hand-held housing and/or osseous limb wrapping. Alternatively, the electrical power source may be external to the hand-held housing and/or osseous limb wrapping.

Further in accordance with an embodiment of the present invention the oscillating element may include an oscillating mass that moves in a periodic motion.

Still further in accordance with an embodiment of the present invention the oscillating element may include an ultrasonic transducer. The vibrating element may vibrate at a frequency in a range of about 1-200 Hz. The vibrating element may induce strain in bone tissue in a range of about 1-500 microstrain.

In accordance with another embodiment of the present invention, the vibrating element may be arranged for seating thereupon.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
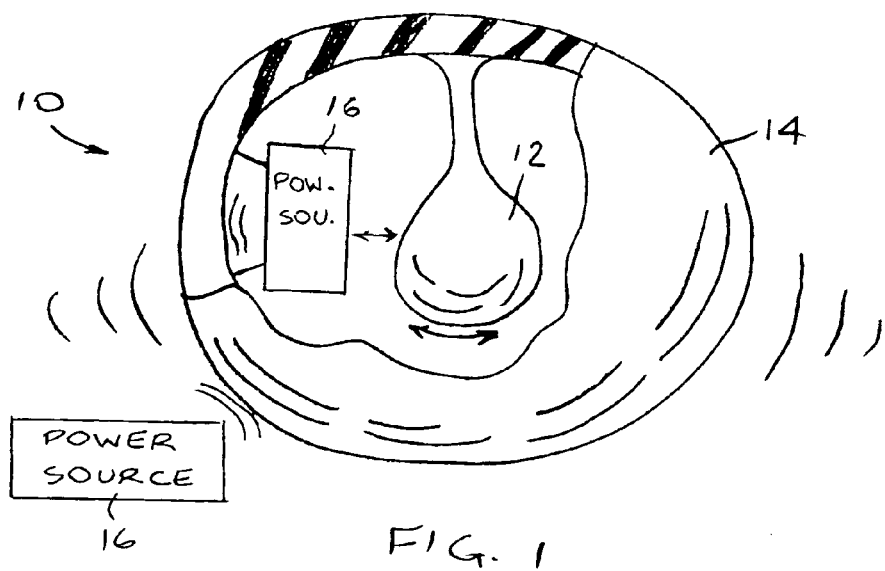
FIG. 1 is a simplified pictorial illustration of a hand-held bone-growth stimulator, constructed and operative in accordance with an embodiment of the present invention.

Reference is now made to FIG. 1, which illustrates a bone-growth stimulator 10, constructed and operative in accordance with an embodiment of the present invention.

The bone-growth stimulator 10 may include a vibrating element 12 housed in a hand-held housing 14. The hand-held housing 14 may be constructed in any shape and of any suitable material. For example, the hand-held housing 14 may be made of an elastomeric material, such as but not limited to, natural or synthetic rubber, silicone rubber or polyurethane, and may be shaped like a sphere or ellipsoid. The vibrating element 12 may include an oscillating element energized by an electrical power source 16. For example, a magnetic weight may be mounted for swinging motion inside the hand-held housing 14 and alternately attracted and repelled by an electromagnetic coil, that is, an oscillating mass that moves in a periodic motion. It is understood that this is just one non-limiting example of vibrating element 12 being energized by electrical power source 16. Other examples include an ultrasonic transducer that induces vibration of a desired amplitude.

The electrical power source 16 may be a battery (which may be rechargeable) disposed in the hand-held housing 14, for example. Alternatively, the electrical power source 16 may be external to the hand-held housing 14, such as but not limited to, mains power or other power supply, and may be in wired (e.g., connected by banana connectors or any other kind of electrical connector or terminal) or wireless (e.g., infrared, BLUETOOTH, RF, etc.) communication with the vibrating element 12.

The vibrating element 12 may vibrate at a frequency in a range of about 1-200 Hz. The vibrating element 12 may induce strain in bone tissue in a range of about 1-500 microstrain. However, the present invention is not limited to these values and other ranges of amplitude and frequency may be used.

The hand-held bone-growth stimulator 10 may maintain or promote bone-tissue growth not only in the bones of the hand and forearm, but may also be effective in other parts of the body, since the vibrations carry to other parts of the body (e.g., bones in the vicinity of the shoulder and chest).

Figure 2:
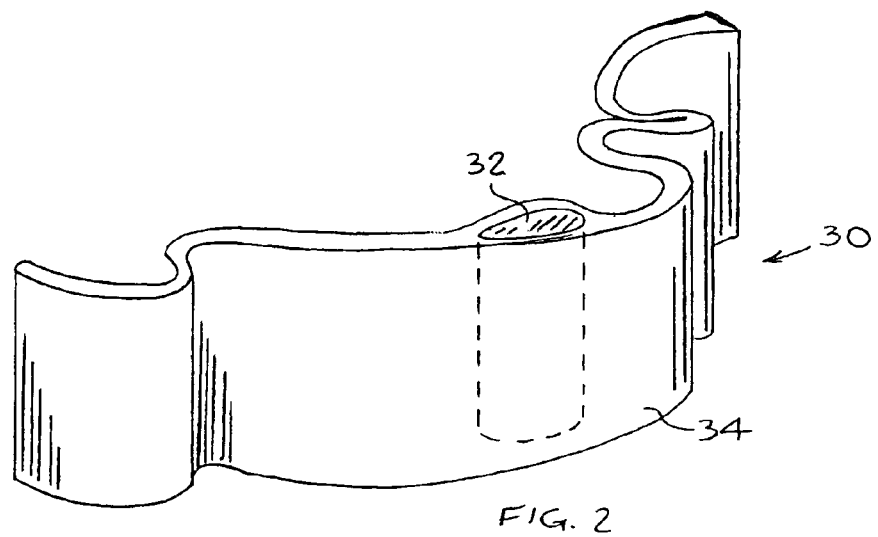
FIG. 2 is a simplified pictorial illustration of a bone-growth stimulator in the form of a wrapping, constructed and operative in accordance with another embodiment of the present invention.

Reference is now made to FIG. 2, which illustrates a bone-growth stimulator 30, constructed and operative in accordance with another embodiment of the present invention. In this embodiment, the bone-growth stimulator 30 may include one or more vibrating elements 32 housed in an osseous limb wrapping 34. By "osseous limb wrapping" it is meant any flexible bandage, strip, blanket and the like, that may be partially or fully wrapped around a bone-containing limb, such as but not limited to, bones of the fingers, hands, toes, feet, legs, hip, ribs, etc. "Partially wrapped" refers to the situation in which the wrapping does not make a full revolution around the perimeter of the limb. "Fully wrapped" refers to the situation in which the wrapping makes one or more revolutions around the perimeter of the limb, wherein the wrappings may be wrapped one on top of the other or next to each other or any combination thereof.

The osseous limb wrapping 34 may be constructed in any shape and of any suitable material. For example, the osseous limb wrapping 34 may be made of an elastomeric material, such as but not limited to, natural or synthetic rubber, silicone rubber or polyurethane, or cloth, woven or non-woven, with one or more pockets for containing the vibrating element 32. Wrapping 34 may be fastened in any manner, such as but not limited to, tying (e.g., laces), VELCRO, hooks (as for an elastic bandage), adhesive, buckles, buttons, zippers and the like. The vibrating element 32 does not have to be received in a pocket or recess, and may be attached in any other manner to wrapping 34, such as but not limited to, by sewing, bonding, embedding, etc. The osseous limb wrapping 34 may have any length, width and thickness. The vibrating element 32 may be as described hereinabove for vibrating element 12.

The wrap-around bone-growth stimulator 10 may maintain or promote bone-tissue growth, and may be effective in the prevention of deep vein thrombosis. The bone-growth stimulator may also assist in the healing of musculoskeletal injuries.

In accordance with yet another embodiment of the present invention, the bone-growth stimulator of the present invention may be placed on a seat, wherein the subject sits on the stimulator. It may also be placed on the arm of the chair so that the patient can place his/her hand on it.

Figure 3:
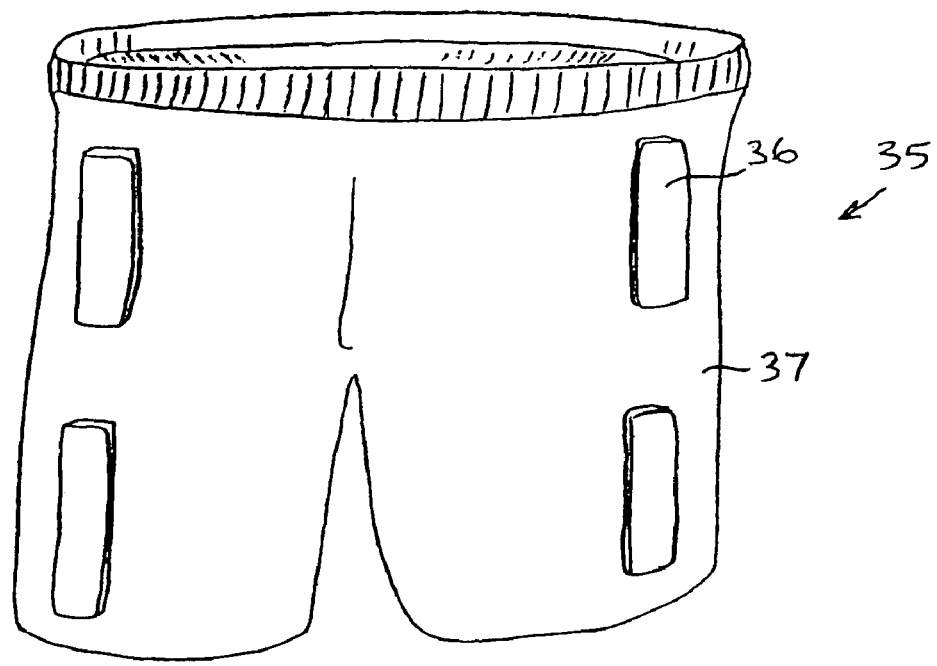
FIG. 3 is a simplified pictorial illustration of a bone-growth stimulator in the form of pants, constructed and operative in accordance with another embodiment of the present invention.

Reference is now made to FIG. 3, which illustrates another bone-growth stimulator 35, constructed and operative in accordance with another embodiment of the present invention. In this embodiment, the bone-growth stimulator 35 may include one or more vibrating elements 36 housed in pants (or trousers or leggings, the terms being used interchangeably) 37. The vibrating elements 36 may be constructed similarly to the embodiment of FIG. 2. The pants 37 are another type of osseous limb wrapping as described in the embodiment of FIG. 2. The bone-growth stimulator 35 may maintain or promote bone-tissue growth in any portion of the leg and hip region, such as but not limited to, the femur, greater trochanters, pelvic bones, etc.

Figure 4:
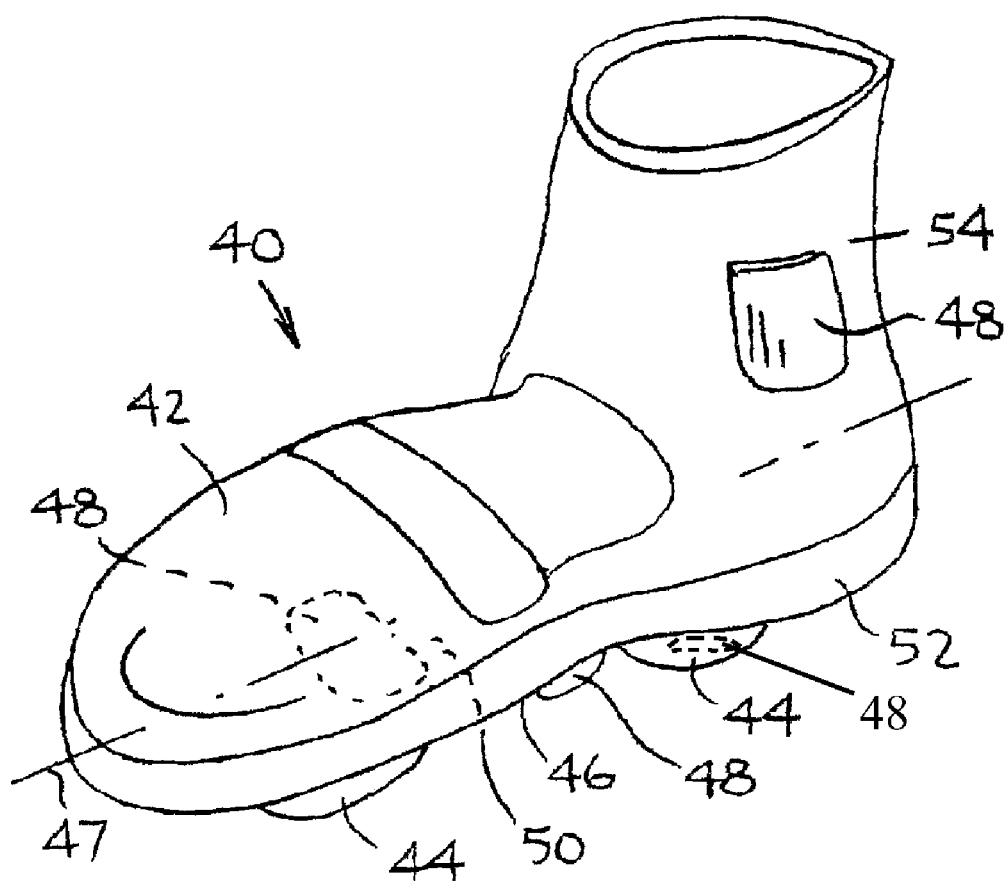
FIG. 4 is a simplified pictorial illustration of a bone-growth stimulator for footwear, constructed and operative in accordance with another embodiment of the present invention.

Reference is now made to FIG. 4, which illustrates a bone-growth stimulator 40 for footwear 42, constructed and operative in accordance with another embodiment of the present invention.

Vibrating massagers for insoles or outer soles of footwear are well known. For example, U.S. Pat. No. 5,913,838 to Reilly describes an insole which can be placed in a user's shoe, and which incorporates vibrators which provide a vibrating massage. The vibrators are connected to a battery operated power supply which can be attached to a user's leg by an elastic strap or attached to a user's shoe by a clip. A wire retraction unit is mounted on the power supply to take up slack in an electrical cable which connects the vibrators and the power supply. In another example, U.S. Pat. No. 5,592,759 to Cox describes an article of footwear made to vibrate by either of two types of vibrating motive members and associated with the structure of the shoe to transmit the vibrations generated to the foot of the wearer. Two vibrating motive members are described, a motor having an off-center shaft-mounted weight and pulsating-type motor.

In the embodiment of FIG. 4, footwear 42 may be as described in published U.S. Patent Application 2004/0033874, wherein the footwear may be used for training, developing and enhancing proprioceptive and kinesthetic skills and neuromuscular control.

Briefly, two bulbous protuberances 44 may protrude from a lower surface 46 of footwear 42. Each protuberance 44 may have a curved outer contour, which may have any curvilinear shape (e.g., generated from a circle, ellipse, parabola or hyperbola). The protuberances 44 may be positioned on a common longitudinal axis 47 of footwear 42.

A vibrating element 48, which may be as described hereinabove for vibrating elements 12 and 32, may be disposed in any portion of footwear 42, such as but not limited to, an insole 50, an outer sole 52 or side wall 54 or any of the protuberances 44, for example.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is clamed is:

1. Apparatus comprising:
   a bone-growth stimulator comprising footwear that comprises a foot-contacting surface for receiving thereupon a user's foot and a ground-contacting surface, wherein two bulbous protuberances, each having a curved outer contour, protrude from a bottom surface of said ground-contacting surface, one of said protuberances being positioned more posteriorly than the other of said protuberances; and
   a vibrating element disposed in at least one of said protuberances.

2. The apparatus according to claim 1, wherein said vibrating element comprises an oscillating element energized by an electrical power source.

3. The apparatus according to claim 2, wherein said oscillating element comprises an oscillating mass that moves in a periodic motion.

4. The apparatus according to claim 2, wherein said oscillating element comprises an ultrasonic transducer.

5. The apparatus according to claim 1, wherein said vibrating element vibrates at a frequency in a range of about 1-800 Hz.

6. The apparatus according to claim 1, wherein said vibrating element is operative to induce strain in bone tissue in a range of about 1-1000 microstrain.

7. The apparatus according to claim 1, wherein said protuberances are positioned on a common longitudinal axis of said footwear.

8. The apparatus according to claim 1, wherein each of said protuberances has said vibrating element disposed therein.

* * * * *